*(12)* United States Patent
Wang et al.

(10) Patent No.: US 8,309,311 B2
(45) Date of Patent: Nov. 13, 2012

(54) METHOD FOR EARLY DETECTION OF CANCERS

(75) Inventors: Hong-Gang Wang, Palmyra, PA (US); Domenico Coppola, Tampa, FL (US)

(73) Assignee: University of South Florida, Tampa, FL (US)

( * ) Notice: Subject to any disclaimer, the term of this patent is extended or adjusted under 35 U.S.C. 154(b) by 84 days.

(21) Appl. No.: 12/730,844

(22) Filed: Mar. 24, 2010

(65) Prior Publication Data

US 2010/0233712 A1 Sep. 16, 2010

Related U.S. Application Data

(63) Continuation of application No. PCT/US2008/077509, filed on Sep. 24, 2008.

(60) Provisional application No. 60/974,638, filed on Sep. 24, 2007.

(51) Int. Cl.
*G01N 33/53* (2006.01)
(52) U.S. Cl. ........................................................ 435/7.1
(58) Field of Classification Search .................... None
See application file for complete search history.

(56) References Cited

U.S. PATENT DOCUMENTS

2006/0281122 A1  12/2006  Bryant et al.

OTHER PUBLICATIONS

Greenbaum et al. (Genome Biology, 2003, vol. 4, Issue 9, pp. 117.1-117.8).*
Takahashi et al (Molecular and Cellular Biology, 2005, 25(21): 9369-9382).*
Tockman et al (Cancer Res., 1992, 52:2711s-2718s).*
Friess et al (Ann Surg, 1999, 230(6): 774-776).*
Lee et al (Pathology, 2006, 38(4): 312-315).*
Lee et al., Decreased Expression of Tumour Suppressor Bax-interacting Factor-1 (Bif-1), a Bax Activator, in Gastric Carcinomas, Pathology, 2006, vol. 38, No. 4, pp. 312-315.
International Search Report for PCT/US08/77509 Dated Dec. 11, 2008.
Nechushtan et al., Bax and Bak Coalesce into Novel Mitochondria-Associated Clusters During Apoptosis, The Journal of Cell Biology, 2001, vol. 153, No. 6, pp. 1265-1276.
Wolter et al., Movement of Bax from the Cytosol to Mitochondria During Apoptosis, The Journal of Cell Biology, 1997, vol. 139, No. 5, pp. 1281-1292.
Griffiths et al., Cell Damage-Induced Confrontational Changes of the Pro-Apoptotic Protein Bak In Vivo Precede the Onset of Apoptosis, The Journal of Cell Biology, 1999, vol. 144, No. 5, pp. 903-914.
Karbowski et al., Endophilin B1 is Required for the Maintenance of Mitochondrial Morphology, The Journal of Cell Biology, 2004, vol. 166, No. 7, pp. 1027-1039.
Takahashi et al., Loss of Bif-1 Suppresses Bax/Bak Conformational Change and Mitochondrial Apoptosis, Molecular and Cellular Biology, 2005, vol. 25, No. 21, pp. 9369-9382.

Lee et al., Loss of Heterozygosity Analysis Defines a Critical Region in Chromosome 1p22 Commonly Deleted in Human Malignant Mesothelioma, Cancer Research, 1996, vol. 56, pp. 4297-4301.
McDavid et al., Prostrate Cancer Incidence and Mortality Rates and Trends in the United States and Canada, Public Health Reports, 2004, vol. 119, pp. 174-186.
Bono, The Global State of Prostate Cancer: Epidemiology and Screening in the Second Millennium, BJU International, 2004, vol. 94, Suppl. 3, pp. 1-2.
Bostwick, Prostatic Intraepithelial Neoplasia Is a Risk Factor for Cancer, Seminars in Urologic Oncology, 1999, vol. 17, No. 4, pp. 187-198.
Chao et al., Epidermal Growth Factor and Serum Activate Distinct Pathways to Inhibit the BH3 Only Protein BAD in Prostate Carcinoma LNCaP Cells, Oncogene, 2006, vol. 25, pp. 4458-4469.
Castilla et al., Bcl-xL Is Overexpressed in Hormone-Resistant Prostate Cancer and Promotes Survival of LNCaP Cells Via Interaction with Proapoptotic Bak, Endocrinology, 2006, vol. 147, No. 10, pp. 4960-4967.
Cuddeback et al., Molecular Cloning and Characterization of Bif-1, The Journal of Biological Chemistry, 2001, vol. 276, No. 23, pp. 20559-20565.
Ming et al., PUMA Dissociates Bax and Bcl-XL to Induce Apoptosis in Colon Cancer Cells, The Journal of Biological Chemistry, 2006, vol. 281, No. 23, pp. 16034-16042.
Aita et al., Cloning and Genomic Organization of Beclin 1, a Candidate Tumor Suppressor Gene on Chromosome 17q21, Genomics, 1999, vol. 59, pp. 59-65.
Emi et al., Correlation of Allelic Losses and Clinicopathological Factors in Primary Breast Cancers, Breast Cancer, 1997, vol. 4, No. 4, pp. 243-246.
Balakrishnan et al., Quantitative Microsatellite Analysis to Delineate the Commonly Deleted Region Ip22.3 in Mantle Cell Lymphomas, Genes, Chromosome & Cancer, 2006, vol. 45, pp. 883-892.
Green et al., A Matter of Life and Death, Cancer Cell, 2002, vol. 1, pp. 19-30.
Bello et al., High-Resolution Analysis of Chromosome Arm 1p Alterations in Meningioma, Cancer Genetics and Cytogenetics, 2000, vol. 120, pp. 30-36.
Kakinuma et al., BCL10 is not a Major Target for Frequent Loss of 1p in Testicular Germ Cell Tumors, Cancer Genetics and Cytogenetics, 2001, vol. 126, pp. 134-138.

(Continued)

*Primary Examiner* — Sean Aeder
(74) *Attorney, Agent, or Firm* — Robert J. Varkonyi; Smith & Hopen, P.A.

(57) ABSTRACT

The invention includes methods for detecting the presence of a neoplastic condition by comparing a sample level of a BIF-1 to a reference, wherein a low level of BIF-1 in the sample correlates with the presence of a neoplastic condition. Another method involves determining the risk of relapse, tumor recurrence and/or metastasis by determining a sample level of a Bif-1 to a reference level of Bif-1, wherein low sample levels correlate with a likelihood of relapse, recurrence and/or metastasis. Yet another method includes detecting the presence of a pre-neoplastic condition, such as prostatic intraepithelial neoplasia. The method involves measuring a level of a Bif-1 in a sample and comparing the level of Bif-1 in the sample to a reference level of Bif-1. High levels of Bif-1 in the sample correlate with the presence of the pre-neoplastic condition.

23 Claims, 1 Drawing Sheet

OTHER PUBLICATIONS

Bonner et al., Molecular Profiling of Mouse Lung Tumors: Association with Tumor Progression, Lung Development, and Human Lung Adenocarcinomas, Oncogene, 2004, vol. 23, pp. 1166-1176.

Gross et al., BCL-2 Family Members and the Mitochondria in Apoptosis, Genes & Development, 1999, vol. 13, pp. 1899-1911.

Knosel et al., Incidence of Chromosomal Imbalances in Advanced Colorectal Carcinomas and Their Metastases, Virchows Arch, 2002, vol. 440, pp. 187-194.

Liang et al., Autophagic and Tumour Suppressor Activity of a a Novel Beclin 1-Binding Protein UVRAG, Nature Cell Biology, 2006, vol. 8, No. 7, pp. 688-699.

Liang et al., Induction of Autophagy and Inhibition of Tumorigenesis by Beclin 1, Nature, 1999, vol. 402, pp. 672-676.

Letai et al., Distinct BH3 Domains Either Sensitize or Activate Mitochondrial Apoptosis, Serving as Prototype Cancer Therapeutics, Cancer Cell, 2002, vol. 2, pp. 183-192.

Levine et al., Development by Self-Digestion: Molecular Mechanisms and Biological Functions of Autophagy, Developmental Cell, 2004, vol. 6, pp. 463-477.

Mora et al., Clinical Categories of Neuroblastoma are Associated with Different Patterns of Loss of Heterozygosity on Chromosome Arm 1p, Journal of Molecular Diagnostics, 2000, vol. 2, No. 1, pp. 37-46.

Pierrat et al., SH3GLB, a New Endophilin-Related Protein Family Featuring and SH3 Domain, Genomics, 2001, vol. 71, pp. 222-234.

Quinn et al., Relationship of Severe Dysplasia to Stage B Adenocarcinoma of the Prostrate, Cancer, 1990, vol. 65, pp. 2328-2337.

Roberts et al., Molecular Characterization of the 1p22 Breakpoint Region Spanning the Constitutional Translocation Breakpoint in a Neuroblastoma Patient with a t(1;10)(p22;q21), Cancer Genetics and Cytogenetics, 1998, vol. 100, pp. 10-20.

Yamaguchi et al., Epothilone B Analogue (BMS-247550)-Mediated Cytotoxicity Through Induction of Bax Conformational Change in Human Breast Cancer Cells, Cancer Research, 2002, vol. 62, pp. 466-471.

Takahashi et al., Bif-1 Interacts with Beclin 1 Through UVRAG and Regulates Autophagy and Tumorigenesis, Nature Cell Biology, 2007, vol. 9, No. 10, pp. 1142-1151.

Walker et al., Deletion Mapping Suggests that the 1p22 Melanoma Susceptibility Gene is a Tumor Suppressor Localized to a 9-Mb Interval, Genes, Chromosomes & Cancer, 2004, vol. 41, pp. 56-64.

Wei et al., Proapoptotic BAX and BAK: A Requisite Gateway to Mitochondrial Dysfunction and Death, Science, 2001, vol. 292, pp. 727-730.

McNeal et al., Intraductal Dysplasia: A Premalignant Lesion of the Prostate, Human Patholology, 1986, vol. 17, No. 1, pp. 64-71.

Sakr et al., High Grade Prostatic Intraepithelial Neoplasia (HGPIN) and Prostatic Adenocarcinoma Between the Ages of 20-69: An Autopsy Study of 249 Cases, In Vivo, 1994, vol. 8, pp. 439-444.

DICTIONARY.COM; "Ratio—Define Ratio at Dictionary.com"; http://dictionary.reference.com/browse/ratio; Accessed on May 10, 2012.

MERRIAM-WEBSTER.COM; "Ratio—Definition and More from the Free Merriam-Webster Dictionary.com"; http://www.merriam-webster.com/dictionary/ratio; Accessed on May 10, 2012.

* cited by examiner

METHOD FOR EARLY DETECTION OF CANCERS

CROSS REFERENCE TO RELATED APPLICATIONS

This application is a continuation of prior filed International Application, Ser. No. PCT/US2008/077509 filed Sep. 24, 2008, which claims priority to U.S. Provisional Application No. 60/974,638, filed Sep. 24, 2007, which are incorporated herein by reference.

GOVERNMENT SUPPORT

This invention was made with government support under grant no. CA82197, awarded by the National Cancer Institute and grant no. RSG-05-244-01-CCG, awarded by the American Cancer Society. The government has certain rights in the invention.

BACKGROUND OF THE INVENTION

This invention relates generally to the early diagnosis and treatment of cancer.

Colorectal adenocarcinoma (CRC) is one of the most common malignancies, accounting for approximately 15% of all cancer-related deaths in the US. The prevalence of CRC increases with age, the largest number of tumors occurring during the sixth decade. The expected annual incidence of this tumor has risen over the last decade and 153,760 new cases are estimated in 2007. If not diagnosed and treated early, this tumor spreads through the entire bowel wall, extends to adjacent organs and eventually metastasizes to regional lymph nodes and distant sites. The majority of deaths from CRC occur in patients with late stage tumors, which are usually incurable.

Programmed cell death (PCD) is defined as a physiological process that plays a critical role in normal development, cellular differentiation and tissue homeostasis of multicellular organisms. Dysregulation of this physiological cell death process contributes to the pathogenesis of human diseases including cancer. In addition to apoptosis (type I cell death), which has long been used as a synonym for PCD, accumulating evidence suggests that autophagy (type II cell death) also belongs to PCD. Autophagy is a highly orchestrated self-digestion process that involves multiple steps from the formation of autophagic vesicles to lysosomal degradation of the vesicles and their contents. As with apoptosis, autophagy also contributes to proper morphogenesis during development and tissue homeostasis in mature organisms.

Inhibition of apoptosis is critical to colorectal tumorigenesis. For example, overexpression of Bcl-XL in cancer may suppress the activity of the proapoptotic molecules Bax and Bak, contributing to cancer progression. It seems that, also in CRC, the dissociation of Bax and Bcl-XL promotes Bax multimerization and mitochondrial translocation, triggering apoptosis. Similarly, dysregulation of autophagy may also play a role in the pathogenesis of cancer. As an example, the autophagy activator Beclin 1 is monoallelically deleted in a high percentage of ovarian, breast, and prostate cancers. Overexpression of Beclin 1 in MCF7 cells promotes autophagy and inhibits tumor formation in nude mice. Moreover, the Beclin 1 binding protein UVRAG promotes autophagy and suppress the tumorigenesis of colon cancer cells in nude mice.

Bif-1 (Bax-Interacting Factor-1) interacts with Bax and induces its conformational change in mammalian cells during apoptosis. Knockout of Bif-1 suppresses Bax/Bak conformational change, cytochrome c release, caspase activation and cell death. The inventors have recently discovered that Bif-1 also regulates autophagy by forming a multi-protein complex with PI3KC3-Beclin1 through UVRAG and loss of Bif-1 suppresses autophagic cell death and promotes tumorigenesis (Takahashi Y, Coppola D, Matsushita N, et al. Bif-1 interacts with Beclin 1 through UVRAG and regulates autophagy and tumorigenesis. Nat Cell Biol 2007; 9: 1142-51 (incorporated herein by reference)). To date the expression of Bif-1 in CRC has not been reported.

SUMMARY OF INVENTION

Here, the inventors show Bif-1 expression and significance in adenocarcinoma cells. Specifically, Bif-1 is down regulated during the transition from normal to adenocarcinoma cells, e.g. the transition from normal colonic mucosa (NR) to colorectal adenocarcinoma cells (CRC). Bif-1 expression levels in CRC were determined using semi-quantitative immunohistochemistry and microarray analysis. Accordingly, the invention includes improved methods for detection of and therapies for neoplastic conditions such as CRC.

In a first embodiment, the invention includes a method for detecting the presence of a neoplastic condition. The method of this embodiment involves measuring a level of a BIF-1 in a sample and comparing the level of BIF-1 in the sample to a reference level of BIF-1. A low level of BIF-1 in the sample correlates with the presence of neoplastic condition.

The method of another embodiment includes determining the risk of relapse, tumor recurrence and/or metastasis related to a neoplastic condition. The method involves determining the level of a Bif-1 in a sample from a patient and comparing the level of Bif-1 in the sample to a reference level of Bif-1. A low level of Bif-1 in the sample correlates with a likelihood of relapse, recurrence and/or metastasis.

Yet another embodiment includes a method of determining the effectiveness of a course of treatment. The method involves determining the level of Bif-1 in a sample from a patient prior to treatment, and determining the level of Bif-1 in a sample after treatment. A higher level of Bif-1 level subsequent to treatment, relative to the biomarker level prior to treatment, indicates the effectiveness of the treatment.

In still another embodiment, the inventors show Bif-1 expression and significance in high grade prostatic intraepithelial neoplasia (PIN), a subset of prostate adenocarcinoma cells. Suprisingly, Bif-1 is over expressed during the transition from normal to adenocarcinoma cells. This result is highly unexpected in light of the pro-apoptotic activity of Bif-1. Bif-1 expression levels in PIN cells were determined using semi-quantitative immunohistochemistry and microarray analysis. Accordingly, the invention includes improved methods for the early detection of a pre-neoplastic condition, such as PIN.

In this embodiment, the invention includes a method for detecting the presence of prostatic intraepithelial neoplasia. The method of this embodiment involves measuring a level of a BIF-1 in a sample and comparing the level of BIF-1 in the sample to a reference level of BIF-1. A high level of BIF-1 in the sample correlates with the presence of prostatic intraepithelial neoplasia.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

In the following detailed description of the preferred embodiments, reference is made to the accompanying drawings, which form a part hereof, and within which are shown by way of illustration specific embodiments by which the invention may be practiced. It is to be understood that other embodiments may be utilized and changes may be made without departing from the scope of the invention.

This invention relates to the finding that expression of Bif-1 can be used to predict clinical outcome for patients with cancer, either independently, or in combination with other biomarkers. As disclosed herein relatively high levels of Bif-1 are found in normal, non-neoplastic, cells. Compared to neoplastic cells, however, Bif-1 immunostaining was pathologically lowered, indicating abnormal under-expression of this pro-apoptotic protein in association with malignant transformation. Here, the expression of Bif-1 was absent in 22.5% of CRC but all of the NR samples were Bif-1 positive. This difference was statistically significant (p=0.002). Remarkably, this trend of Bif-1 protein expression down regulation in CRC was mirrored by significant decrease in the mRNA levels of Bif-1 at an early stage of colorectal cancer development. Since loss of Bif-1 not only suppresses Bax/Bak activation and apoptosis but also inhibits PI3KC3 activation and autophagy.

Bif-1, also known as endophilin B1 and SH3GLB1 (SH3 domain GRB2-like endophilin B1), was originally identified as a Bax-binding protein by yeast two-hybrid screens using Bax as the bait. The human Bif-1 gene encodes a 365 amino-acid polypeptide that contains an N-terminal BAR (Bin/Amphiphysin/Rvs) domain, a central coiled-coil domain, and a C-terminal SH3 domain. The N-terminal part (1-27 amino acids) of Bif-1 is required for its binding to Bax. Moreover, the interaction between Bif-1 and Bax is enhanced in mammalian cells during apoptosis, which is accompanied by a conformational change in the Bax protein.

Overexpression of Bif-1 promotes Bax activation and apoptosis, whereas inhibition of Bif-1 expression suppresses Bax/Bak conformational activation, cytochrome c release, caspase activation and cell death in response to intrinsic apoptosis signals. Bif-1 regulates apoptosis by mediating the mitochondrial fission process.

Besides its role as a Bax activator, Bif-1 is also involved in autophagosome formation and autophagic cell death. Bif-1 interacts with Beclin 1 through UVRAG to positively regulate the class III PI3-kinase (PI3KC3) lipid kinase during autophagy. Although the C-terminal SH3 domain of Bif-1 is sufficient for binding to UVRAG, the N-terminal BAR domain of Bif-1 is also required for Bif-1 to activate PI3KC3 lipid kinase and induce autophagosome formation. Suppression of Bif-1 expression inhibits autophagy and prolongs cell survival under nutrient starvation. Moreover, Bif-1 ablation promotes the development of spontaneous tumors in mice, consistent with the notion that both apoptosis and autophagy play crucial roles in tumor suppression.

Bif-1 mRNA levels are downregulated in lung carcinomas, and that approximately 60% gastric carcinomas express undetectable levels of Bif-1 protein. In addition, loss of heterozygosity (LOH) on 1p22, where the bif-1 gene is localized, is frequently observed in many types of tumor. In CRC 1p22 deletions were identified in >70% of advanced stage and metastatic tumors. These results are in agreement with other studies showing that 1p deletion was significantly more common in metastatic as compared to primary CRC. Others have described a 38% incidence of 1p deletions in 34 sporadic colorectal adenomas, using a centromeric probe for chromosome 1 and a simultaneous telomeric probe mapping to 1p36.

As used herein, the term "neoplastic condition" refers to a class of diseases characterized by the uncontrolled growth of aberrant cells, whether such condition is characterized as malignant, benign, soft tissue or solid tumor. Specific neoplastic conditions include digestive and gastrointestinal cancers, such as anal cancer, bile duct cancer, gastrointestinal carcinoid tumor, colon cancer, esophageal cancer, gallbladder cancer, liver cancer, pancreatic cancer, rectal cancer, appendix cancer, small intestine cancer and stomach (gastric) cancer; breast cancer; ovarian cancer; lung cancer; renal cancer; CNS cancer; leukemia and melanoma. In a preferred embodiment, the term "neoplastic condition" refers to colorectal adenocarcinoma.

As used herein, the term "level" refers to mean the amount, accumulation or rate of a biomarker molecule, such as Bif-1. A level can be represented, for example, by the amount or synthesis rate of messenger RNA (mRNA) encoded by a gene, the amount or synthesis rate of polypeptide corresponding to a given amino acid sequence encoded by a gene, or the amount or synthesis rate of a biochemical form of a molecule accumulated in a cell, including, for example, the amount of particular post-synthetic modifications of a molecule such as a polypeptide, nucleic acid or small molecule. The term can be used to refer to an absolute amount of a molecule in a sample or to a relative amount of the molecule, including amounts determined under steady-state or non-steady-state conditions. The expression level of a molecule can be determined relative to a control molecule in a sample.

A gene expression level of a molecule refers to the amount, accumulation or rate of synthesis of a biomarker gene. The gene expression level can be represented by, for example, the amount or transcription rate of mRNA encoded by a gene. A gene expression level similarly refers to an absolute or relative amount or a synthesis rate determined, for example, under steady-state or non-steady-state conditions.

A polypeptide expression level refers to the amount, accumulation or rate of synthesis of a biomarker polypeptide. The polypeptide expression level can be represented by, for example, the amount or rate of synthesis of the polypeptide, a precursor form or a post-translationally modified form of the polypeptide. Various biochemical forms of a polypeptide resulting from post-synthetic modifications can be present in cell contained in a sample.

As used herein, the term "reference level" refers to a control level of expression of a biomarker used to evaluate a test level of expression of a biomarker in a sample. For example, when the level of Bif-1 in the neoplastic cells of a patient is lower than the reference level of Bif-1, the cells will be considered to have a low level of expression, or underproduction, of Bif-1. Conversely, when the level of Bif-1 in the neoplastic cells of a patient are higher than the reference level, the cells will be considered to have a high level of expression, or overproduction, of Bif-1.

The reference level can be determined by a plurality of methods, provided that the resulting reference level accurately provides a level of a biomarker above which exists a first group of patients having a different probability of survival than that of a second group of patients having levels of the biomarker below the reference level. The reference level can be determined by, for example, measuring the level of expression of a biomarker in tumorous or non-tumorous cancer cells from the same tissue as the tissue of the neoplastic cells to be tested. The reference level can also be a level of a biomarker of in vitro cultured cells, which can be manipulated to simulate tumor cells, or can be manipulated in any other manner that yields expression levels, which accurately determine the reference level.

The reference level can also be determined by comparison of the level of a biomarker, such as Bif-1, in populations of patients having the same cancer. Two or more separate groups of patients can be determined by identification of subsets populations of the cohort that have the same or similar levels of the biomarker. Determination of the reference level can then be made based on a level which best distinguishes these separate groups. A reference level also can represent the levels of two or more markers. Two or more markers can be represented, for example, by a ratio of values for levels of each biomarker.

The reference level can be a single number, equally applicable to every patient, or the reference level can vary, according to specific subpopulations of patients. For example, older men might have a different reference level than younger men for the same cancer, and women might have a different reference level than men for the same cancer. Furthermore, the reference level can be some level determined for each patient individually. For example, the reference level might be a certain ratio of a biomarker in the neoplastic cells of a patient relative to the biomarker levels in non-tumor cells within the same patient. Thus, the reference level for each patient can be proscribed by a reference ratio of one or more biomarkers, such as Bif-1, wherein the reference ratio can be determined by any of the methods for determining the reference levels described herein.

The reference level can also represent the level of a biomarker protein, such as Bif-1, in one or more compartments of the cell. Typically, the reference level will represent the level of biomarker protein in the whole cell, the nucleus or the cytosol. This level will be useful when cell compartmentalization of the protein correlates with the risk of tumor recurrence or spread of a certain cancer. Similarly, the reference level can be a ratio of levels of biomarker protein in the different compartments (for example, the ratio of nuclear biomarker protein to whole cell biomarker protein, or the ratio of nuclear to cytosolic biomarker protein).

As used herein, the term "sample" refers to any biological fluid, cell, tissue, organ or portion thereof, such as a cell from the colon, rectum, breast, ovary, prostate, kidney, lung, blood, brain or other organ or tissue that contains or is suspected to contain a neoplastic cell. The term includes samples present in an individual as well as samples obtained or derived from the individual. For example, a sample can be a histologic section of a specimen obtained by biopsy, or cells that are placed in or adapted to tissue culture. A sample further can be a subcellular fraction or extract, or a crude or substantially pure nucleic acid molecule or protein preparation.

Therefore, in one embodiment, the invention includes a method for detecting the presence of a neoplastic condition. The method involves (a) measuring a level of a Bif-1 in a sample, and (b) comparing the level of Bif-1 in the sample to a reference level of Bif-1, wherein low levels of Bif-1 in the sample correlate with the presence of a neoplastic condition.

A level of Bif-1 in a sample that is lower than a determined basal level, or reference level, of Bif-1 can be a significant factor in tumor development, recurrence or spread. When reference levels are lower than the level of Bif-1 in the sample, the level of Bif-1 is characterized as low or under expressed. Low or under expressed Bif-1 levels are indicative of increased risk of tumor recurrence or spread. Normal Bif-1 can be indicative of decreased risk of tumor development, recurrence or spread.

The level of Bif-1 can be determined by measuring the amount of a biomarker mRNA or DNA using a binding agent selective for the biomarker, such as a nucleic acid probe. The methods used to detect mRNA levels include detection of hybridization or amplification of mRNA encoding the biomarker. This detection can be carried out by analysis of mRNA either in vitro or in situ using one of the methods known to one of ordinary skill in the art. A Bif-1 mRNA, or other biomarker mRNA, detected will be any RNA transcript of a Bif-1 gene, or fragment thereof.

In an alternate embodiment, the invention includes a method for detecting the presence of a pre-neoplastic condition, such as prostatic intraepithelial neoplasia. The method involves (a) measuring a level of a Bif-1 in a sample, and (b) comparing the level of Bif-1 in the sample to a reference level of Bif-1, wherein high levels of Bif-1 in the sample correlate with the presence of the pre-neoplastic condition.

When reference levels are greater than the level of Bif-1 in the sample, the level of Bif-1 is characterized as high or over expressed. High or over expressed Bif-1 levels are indicative of increased risk of developing a neoplastic condition, such as prostate cancer. Normal Bif-1 can be indicative of decreased risk.

The level of Bif-1 can be determined by measuring the amount of a biomarker mRNA or DNA using a binding agent selective for the biomarker, such as a nucleic acid probe. The methods used to detect mRNA levels include detection of hybridization or amplification of mRNA encoding the biomarker. This detection can be carried out by analysis of mRNA either in vitro or in situ using one of the methods known to one of ordinary skill in the art. A Bif-1 mRNA, or other biomarker mRNA, detected will be any RNA transcript of a Bif-1 gene, or fragment thereof.

The diagnostic methods of the invention are useful for determining if a patient is at risk for relapse. Cancer relapse is a concern relating to a variety of types of cancer. One explanation for cancer recurrence is that patients with relatively early stage disease (for example, stage II or stage III) already have small amounts of cancer spread outside the affected tissue. These cancer cells, referred to as micrometastases, cannot typically be detected with currently available tests.

The diagnostic methods of the invention can be used to identify surgically treated patients likely to experience cancer recurrence or relapse so that they can be offered additional therapeutic options, including preoperative or postoperative adjuncts such as chemotherapy, radiation, biological modifiers and other suitable therapies. As used herein, the term "risk of recurrence" refers to the probability of tumor recurrence or spread in a patient subsequent to diagnosis of cancer, wherein the probability is determined according to the process of the invention. Tumor recurrence refers to further growth of neoplastic or cancerous cells after diagnosis of cancer. Particularly, recurrence can occur when further cancerous cell growth occurs in the cancerous tissue. Tumor spread refers to dissemination of cancer cells into local or distant tissues and organs, for example during tumor metastasis. Tumor recurrence, in particular, metastasis, is a significant cause of mortality among patients who have undergone surgical treatment for cancer.

The methods are especially effective for determining the risk of metastasis in patients who demonstrate no measurable metastasis at the time of examination or surgery. The method involves (a) determining the level of a Bif-1 in a sample from a patient after receiving treatment, and (b) comparing the level of Bif-1 in the sample to a reference level of Bif-1, wherein low levels of Bif-1 in the sample correlate with a likelihood of relapse, recurrence and/or metastasis.

When cancer recurrence is likely, it can be advantageous to precede or follow surgical treatment with chemotherapy, radiation, immunotherapy, biological modifier therapy, gene therapy, vaccines and the like, or adjust the span of time during which the patient is treated. Therefore, the diagnostic methods of the invention also are useful for determining the effectiveness of a course of treatment. A course of treatment refers to the therapeutic measures taken for a patient after diagnosis or after treatment for cancer. As used in the context of a course of treatment, "effectiveness" refers to the ability of the course of treatment to decrease tumor size, risk of recurrence or spread and therefore to increase the likelihood of disease-free or overall survival of the patient. Comparison of biomarker levels in a sample from a patient before and after treatment will thereby serve to indicate whether a biomarker level is returning to that of non-tumor cells, implying a more effective course of treatment, or whether a biomarker level is remaining abnormal or increasing in abnormality, implying a less effective course of treatment. For example, a decrease in the level of Bif-1 in a patient sample after treatment indicates that treatment is ineffective because low levels of Bif-1 correlate with an increased risk of cancer recurrence.

Accordingly, a high or increased level of Bif-1 in a patient sample after treatment indicates that treatment is effective because higher levels of Bif-1 correlate with a lower incidence cancer recurrence. The method involves (a) determining the level of a Bif-1 in sample prior to treatment, and (b) determining the level of Bif-1 in a sample after treatment, whereby comparison of the Bif-1 level prior to treatment with the biomarker level after treatment indicates the effectiveness of the treatment.

It is understood that modifications which do not substantially affect the activity of the various embodiments of this invention are also included within the definition of the invention provided herein. Accordingly, the following examples are intended to illustrate but not limit the present invention.

EXAMPLE I

Tissue samples (140: 102 CRC and 38 samples of normal colonic mucosa (NR)) were analyzed for Bif-1 expression by immunohistochemistry using stage oriented human colorectal cancer tissue microarrays (prepared in the Histology laboratory of the Moffitt Cancer Center Tissue Core Facility). All tumors used for the tissue array construction were CRC identified from the Moffitt Cancer Center Anatomic Pathology Division's database, CoPath®, representing surgical resection specimens obtained between 1990 and 2002. All of the specimens were preserved in 10% buffered formalin prior to embedding in paraffin. The patients had a median age of 65 years (range 24-92), 61 were male and 41 were female. The tumors ranged in size between 1.4 cm and 14.5 cm.

The tumors were staged according to the TNM system, following the recommendations of the American Joint Committee on Cancer, 1988. The stage of the invasive tumors was as follows: 10 patients had stage I (Duke's stage A), 33 stage II (Duke's stage B), 38 stage III (Duke's stage C), and 21 stage IV (Duke's stage D). All tumors occurred in the absence of genetic cancer syndromes such as human non-polyposis colon cancer syndrome (HNPCC), familial adenomatous polyposis syndrome (FAP), etc.; also, cancers arising in the background of ulcerative colitis or Crohn's disease were excluded from the study. The NR samples were taken near the resected colorectal margin, away from the tumor site, from the CRC colon resection specimens.

The tissues were stained for Bif-1, using a mouse monoclonal antibody (Imgenex, San Diego, Calif.). The slides were dewaxed by heating at 55° C. for 30 minutes and by three washes, five minutes each, with xylene. Tissues were rehydrated by a series of five-minute washes in 100%, 95% and 80% ethanol, and distilled water. Endogenous peroxidase activity was blocked with 3% hydrogen peroxide for 20 minutes. After blocking with universal blocking serum (Ventana Medical Systems, Inc., Tucson, Ariz.) for 30 minutes, the samples were incubated with anti-Bif-1 mouse monoclonal antibody (Imgenex, dilution 1:2500) at 4° C. overnight. The samples were then incubated with biotin-labeled secondary antibody and streptavidin-horseradish peroxidase for 30 minutes each (Ventana Medical Systems). The slides were developed with 3,3'-diaminobenzidine tetrahydrochloride substrate (Ventana Medical Systems Inc.) and counterstained with hematoxylin (Ventana Medical Systems Inc. Tucson, Ariz.). The tissue samples were dehydrated and coversliped. Standard cell conditioning (following the Ventana proprietary recommendations) was used for antigen retrieval. The specificity of the anti-Bif-1 monoclonal antibody was confirmed by immunostains of Bif-1 overexpression and knockout cell lines. Negative control was included by using non-immune mouse sera and omitting the monoclonal Bif-1 antibody during the primary antibody incubation step.

The Bif-1 stained tissue cores were examined by two independent observers simultaneously and a consensus score was reached for each specimen. The positive reaction of Bif-1 was scored into four grades, according to the intensity of the staining: 0, 1+, 2+ and 3+. The percentages of Bif-1 positive cells were also scored into four categories: 0 (0%), 1 (1-33%), 2 (34-66%), and 3 (67-100%). The product of the intensity by percentage scores was used as the final score. The final scores were classified as: 0 negative; 1-3, weak; 4-6, moderate; and 7-9, strong. The specimens were also classified by the types of tissue staining positive: normal colonic mucosa and adenocarcinoma.

Descriptive statistics for the scores were generated and reported for each tissue group. The initial method used to compare Bif-1 expression in CRC and NR was the Wilcoxon Rank sum test. In addition, Fisher's exact test was used to compare Bif-1 negativity between CRC and NR. For CRC the exact Cochran-Armitage trend test was used to compare Bif-1 negativity across stage. The Holm step down method was used to adjust for multiple testing. Age and gender differences between cohorts were examined using the Wilcoxon rank sum test and the Chi-square test, respectively. Spearman's correlation was used to examine the correlation between age and Bif-1 expression, and the Wilcoxon rank sum test was used to compare Bif-1 expression differences between genders.

Clinical pathologic findings. The patients had a median age of 65 years (range, 24-92). Sixty-one were male and 41 were female. The tumors ranged in size between 1.4 cm and 14.5 cm, mostly polypoid and ulcerated. Twenty tumors involved the cecum, 26 the ascending colon, 4 the transverse colon, 9 the descending colon, 24 the sigmoid, 10 the rectosigmoid junction, and 9 the rectum. Fourteen tumors were well differentiated, 74 moderately differentiated, and 14 poorly differentiated. Ten tumors were Duke's stage A, 33 Duke's stage B, 38 Duke's stage C, and 21 Duke's stage D. Only 2 patients, both with rectal cancer, received preoperative radiation, to decrease the size of their tumors.

Immunohistochemical observations. All of the positively stained cases had cytoplasmic staining, which was diffusely granular with variation in intensity seen within the same lesion of some cases. Cases with variable staining were graded based on the predominant staining intensity and the percentage of positive stain was determined based on the amount of the lesion demonstrating the predominant intensity. In CRC specimens, approximately 41.2% (42/102) had weak Bif-1 staining, 36.3% (37/102) exhibited moderate to strong Bif-1 staining, and 22.5% (23/102) were Bif-1 negative. In contrast, in NR samples, 68.4% (26/38) exhibited moderate to strong Bif-1 immunoreactivity, 31.6% (12/38) showed weak Bif-1 staining and none was Bif-1 negative. The specificity of the anti-Bif-1 antibody was confirmed by immunostaining of Bif-1 over expressing cells as compared to the Bif-1 knockout cell line.

Statistical analysis. There was a statistically significant difference found in Bif-1 staining score between NR and CRC, using the Wilcoxon rank sum test (p=0.0003), and there was also a significant difference in Bif-1 negativity (p=0.002) when comparing the percentage negative (as dichotomous groups) between the two tissue types. Using the exact Cochran-Armitage trend test, there was no statistically significant increasing trend between Bif-1 negativity score and tumor stage (p-value=0.29). When considering the expression of Bif-1 in the NR versus the CRC it became evident that while 22.5% of CRC were negative, none of the NR was negative. This difference was statistically significant (p=0.002). There were no statistically significant differences found in age or gender between the NR and CRC cohorts (p=0.39 and p=0.63, respectively: Table 1), and age and gender were not found to be significantly correlated with Bif-1 staining score (p=0.68 and p=0.26, respectively).

TABLE 1

|  | Normal (n = 38) | CA (n = 102) | p-value |
|---|---|---|---|
| Gender |  |  |  |
| Male | 21 (55.3%) | 61 (59.8%) |  |
| Female | 17 (44.7%) | 41 (40.2%) | 0.63* |
| Age |  |  |  |
| Median | 68 years | 65 years |  |
| Range | (34-91 years) | (24-92 years) | 0.39** |

*Chi-square test.
**Wilcoxon rank sum test

EXAMPLE II

Two hundred and five (205) colorectal adenocarcinoma tumor specimens and 10 samples of normal colorectal mucosa, from patients treated at the Moffitt Cancer Center under a University of South Florida IRB-approved protocol were arrayed on Affymetrix HG-U133+ GeneChip microarrays to evaluate whether the variation in Bif-1 protein expression between NR and CRC reflected a corresponding modulation of Bif-1 mRNA. The tumors, used for the mRNA microarray analysis, included mirror image samples from all of the CRC used to construct the colon tissue microarray (TMA) utilized in this study.

The data was processed using MAS5.0 and scaled to a mean intensity of 500. Three probe sets were identified by Affymetrix NetAffx as detecting Bif-1: 209090_s_at, 209091_s_at and 210101_x_at. The R statistical software was used for expression analysis (freely available open source statistical package: Institute for Statistics and Mathematics, WU Wirtschaftsuniversität Wien, Vienna Austria). The Anderson-Darling test for normality was used to verify the distribution of gene expression for each probe set across samples and a t test was used to compare differences between groups (normal vs. tumor and normal vs. each stage). Expression is graphed using the mean and standard error for each probe set across the different groups.

Figure 1:
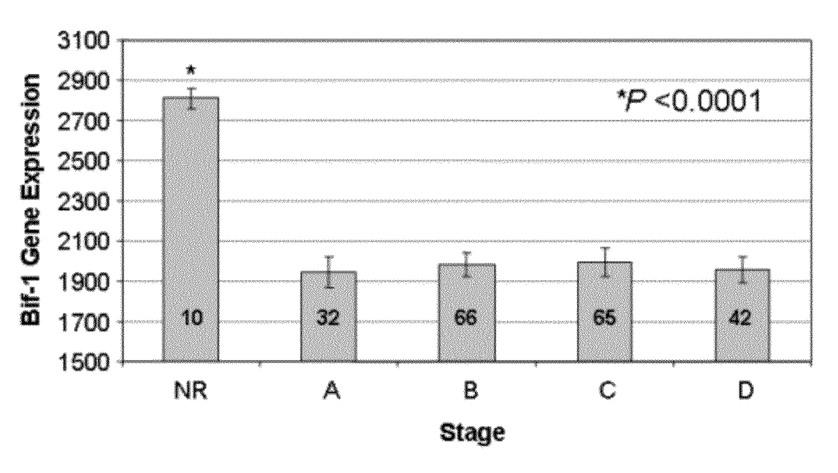
The FIGURE is a graph showing Bif-1 mRNA expression is downregulated in human colorectal tumors. The mRNA levels of Bif-1 were analyzed by DNA microarray in 10 NR and 205 CRC (32 stage A, 66 stage B, 65 stage C, and 42 stage D) samples. The data shown are means±standard deviations.

Gene profiling. To determine whether Bif-1 changes in protein level during human colorectal cancer development reflect changes in gene expression, we compared the Bif-1 mRNA levels by DNA microarray in 10 normal human colon tissues and 205 colorectal tumors grouped by Dukes' staging system. The samples included 32 stage A, 66 stage B, 65 stage C, and 42 stage D colorectal adenocarcinomas. The expression of Bif-1 mRNA decreased significantly between NR and stage A CRCs and kept about the same levels during tumor progression (The FIGURE), suggesting that loss of Bif-1 expression may play a role at an early stage of colorectal tumorigenesis

EXAMPLE III

High grade prostatic intraepithelial neoplasia (PIN) is the putative premalignant lesion of prostatic adenocarcinoma, and it is characterized by the proliferation of high grade dysplastic cell within the prostatic acini and duct. PIN has been reported to be a risk factor for subsequent detection of adenocarcinoma. High grade PIN is usually seen adjacent to or intermingled with prostatic adenocarcinoma in up to 75% of cases, and that large areas of high grade PIN may be associated with microinvasive carcinoma. In addition, it seems that, similarly to what is observed with adenocarcinoma, the incidence of high grade PIN increases with age.

This embodiment focuses on the evaluation of Bif-1 expression and significance in prostatic hyperplasia, high grade PIN and prostatic adenocarcinoma. Expression of Bif-1 was found in 89.9% of the normal prostate samples studied. Bif-1 protein was absent in 17.2% (33/192) of the total number of prostate cancer examined. These findings support the pro-apoptotic and tumor suppressor functions of Bif-1.

However, Bif-1 protein expression was increased in a subset of tumors. In particular, the highest Bif-1 expression was found in PIN, a precursor of prostatic adenocarcinoma. In prostatic cancer, the expression of Bif-1 persisted but at a lower level compared to that in PIN, and the difference in Bif-1 score between PIN and CA was statistically significant in both the non TMA samples (p=0.0171) and in the TMA samples (p=0.003). This example demonstrates for the first time that Bif-1 is highly expressed during the progression of prostate adenocarcinoma.

One possibility is that Bif-1 may play an important role in the early stages of prostate tumor development. For example, transformed prostate acinar cells are upregulating Bif-1 expression in a tentative to induce apoptosis of these abnormal cells. In addition to its pro-apoptotic function, we have recently discovered that Bif-1 plays a critical role in autophagy as a positive regulator of autophagosome formation. Autophagy is a self-eating process connected to cell survival by supplying the cell with recycled nutrients under starvation condition. Therefore, Bif-1 overexpression in PIN may be a mechanism to induce autophagy by which the cell is trying to survive the environmental stresses associated with limited angiogenesis and nutrition. Once the tumor is established the function of Bif-1 as an activator of autophagy is no longer required, but its expression may persist as a mechanism to counteract tumor growth.

Pathology specimens (paraffin embedded tissue) of 39 prostatic adenocarcinomas, were identified from the H. Lee Moffitt Cancer Center Anatomic Pathology Division's database, CoPath®, for surgical specimens obtained between 2000 and 2006. The patients selected for this study did not undergo pre-operative neoadjuvant therapy as part of their treatment. The selected blocks included adjacent areas of prostatic hyperplasia in 27 of the cases, and high grade PIN in 32 of the cases.

In addition, human prostate cancer tissue microarray (TMA), prepared in the Histology Laboratory of the Moffitt Cancer Center Tissue Core Facility, were also tested for Bif-1 expression. The prostate TMA included 19 samples of normal prostate (NR), 26 samples of benign prostatic hyperplasias (BPH), 30 samples of prostatic intraepithelial neoplasia (PIN), and 153 samples of prostate carcinoma.

When considered together, TMA and resection specimens accounted for 19 cases of NR, 58 cases of BPH, 57 cases of PIN, and 192 prostatic cancer samples.

All of the specimens were preserved in 10% buffered formalin prior to embedding in paraffin. The tissue sections were stained to assess the variations in Bif-1 expression during the progression from normal prostate to hyperplasia, to prostatic intraepithelial neoplasia, to carcinoma.

Immunohistochemistry: Unstained tissue sections were cut from representative blocks of the formalin-fixed, paraffin embedded tissues of thirty nine resection specimens, as well as from the prostate TMA block. These sections were mounted on slides and stained for Bif-1, using a mouse monoclonal antibody (Imgenex, San Diego, Calif.).

The slides were dewaxed by heating at 55° C. for 30 minutes and by three washes, five minutes each, with xylene. Tissues were rehydrated by a series of five-minute washes in 100%, 95%, and 80% ethanol, and distilled water. Endogenous peroxidase activity was blocked with 3% hydrogen peroxide for 20 minutes. After blocking with universal blocking serum (Ventana Medical Systems, Inc., Tucson, Ariz. OMNIMAP) for 30 minutes, the samples were incubated with a Bif-1 mouse anti-human monoclonal antibody (Imgenex, dilution 1:2500; final concentration of 1 µg/ml) at 4° C. overnight. The sections were then incubated with biotin-labeled secondary antibody and streptavidin-horseradish peroxidase for 30 minutes each (Ventana Medical Systems). The samples were developed with 3,3'-diaminobenzidine tetrahydrochloride substrate (Ventana Medical Systems Inc. Tucson, Ariz.) and counterstained with hematoxylin (Ventana Medical Systems Inc. Tucson, Ariz., product #760-2021). The slides were dehydrated and coversliped. Standard cell conditioning (following the Ventana proprietarian recommendations) was used for antigen retrieval. Negative controls were included by omitting Bif-1 antibody during the primary antibody incubation. The positive controls consisted of a cytospin preparation of cells constitutively expressing Bif-1 protein.

Statistical analysis: The Bif-1 stained slides were examined by two independent observers simultaneously; and a consensus score was reached for each specimen. The positive reaction of Bif-1 was scored into four grades, according to the intensity of the staining: 0, 1+, 2+, and 3+. The percentages of Bif-1 positive cells were also scored into four categories: 0 (0%), 1 (1-33%), 2 (34-66%), and 3 (67-100%). The product of the intensity by percentage scores was used as the final score. The final scores were classified as: 0 negative; 1-3, weak; 4-6, moderate; and 7-9, strong. The specimens were also classified by the types of tissue staining positive: normal prostate, prostatic hyperplasia, high grade prostatic intraepithelial neoplasia, and prostatic adenocarcinoma.

Descriptive statistics for the scores obtained from the non-TMA samples were generated and reported for each group. The statistical method used to compare the scores by groups was the Wilcoxon Signed Rank test. Three tests were performed and a Bonferroni-Holm adjustment for multiple testing was performed to correct for multiple testing, using SAS software (SAS Institute Inc., Cary, N.C.). Comparisons were done for 1) CA versus PIN, 2) CA versus BPH and 3) PIN versus BPH. Spearman's correlation coefficient was used to analyze the relationship between Bif-1 expression and Gleason's grading score.

The analysis on the TMA data was included as a follow-up, confirmatory analysis to the original BIF analysis. The method used to compare Bif-1 expression in CA, PIN, BPH and NR is the Wilcoxon Rank sum test since the data in this TMA portion of the study was not paired data. Six tests were performed and a Bonferroni-Holm adjustment for multiple testing was used to correct for multiple testing.

Clinical Pathologic Findings: When considering the non-TMA specimens, the patients had an average age of 60 years (range between 42 and 85 years old). Six of the cases were metastatic resections (4 cases of lymph nodes excision, 1 local excision of chest wall tumor, and 1 excisional biopsy of a tumor of the posterior bladder wall). Thirty-three cases were primary tumor resection. These tumors ranged in size between 0.4 cm. and 2.5 cm, mostly multifocal and bilateral. The most common Gleason score was 7 (16 cases), followed by 6 (8 cases), 9 (5 cases), and 8 (4 cases). Twenty-three patients had stage II, 10 had stage III, and 6 had stage IV disease. All the patients were treated with surgery: excision or resection for the metastases, and radical retropubic prostatectomy for the primary tumors. Twenty-seven patients were treated with surgery alone; twelve patients received additional therapy: radiation (3), chemotherapy (2), or both (2), hormonal therapy (1), radiation, chemotherapy and hormonal therapy (2), hormonal plus radiation (1) and hormonal plus chemotherapy (1). All additional therapy was administered postoperatively (adjuvant therapy). The patients were followed up between 8 to 98 months. The mean follow-up time of all patients was 30.5 months. At the end of the study 32 patients were alive with no evidence of disease (mean follow-up of 31 months) 1 patient was dead of disease (follow-up of 27 months), two were alive with disease (mean follow-up of 44 mo.), and 4 patients were lost to follow up. Since there was only one event, a survival analysis with respect to Bif-1 expression was not informative.

Immunohistochemical results and data analysis: All of the positively stained cases had cytoplasmic staining Nuclear staining by Bif-1 was not seen. The cytoplasmic staining was diffusely granular with variation in intensity seen within the same lesion in some cases. Cases with variable staining were graded based on the predominant staining intensity and the percentage of positive stain was determined based on the amount of the lesion demonstrating the predominant intensity.

Of the non-TMA cases, approximately 72% (28/39) of the prostatic adenocarcinomas exhibited strong Bif-1 staining, and 26% (10/39) of patients demonstrated moderate Bif-1 staining. The mean score was 6.7 (2.0 s.d.) for adenocarcinoma. Similarly, 91% (29/32) cases of high-grade prostatic intraepithelial neoplasia demonstrated strong Bif-1 staining. The mean score was 7.2 (2.1 s.d.) for high grade PIN. Only 1 of the adenocarcinoma and none of the high grade PIN had weak Bif-1 expression. There was no discernable difference in Bif-1 expression in adenocarcinomas with different Gleason's grading score (Spearman's correlation coefficient: −0.054; p value=0.76). When comparing the difference in the staining scores between high grade PIN and adenocarcinoma, a p-value of 0.0171 was calculated.

No cases of carcinomas and/or high grade PIN were Bif-1 negative. Most of the prostatic hyperplasia (88.9%; 24/27) exhibited weak Bif-1 staining. The mean score was 2.0 (1.2 s.d.) for prostatic hyperplasia. Moderate Bif-1 stain was only observed in 3 of 27 cases (11%). When comparing the differences in the staining scores between adenocarcinomas and hyperplasia, a p-value of <0.0001 was calculated. A similar value was calculated when comparing high grade PIN to prostatic hyperplasia.

When considering the TMA cases, 38.6% (59/153) of CA showed moderate to strong Bif-1 expression, 39.8% (61/153) had weak Bif-1 staining, and 21.5% (33/153) were Bif-1 negative. The CA mean score was 3.5 (2.9 s.d.). Bif-1 expression in PIN was strong in 16.6% (5/30), moderate in 60% (18/30), and weak in 20% (6/30) of cases. Only one PIN case was Bif-1 negative. The PIN mean score was 5.3 (2.4 s.d.). When considering BPH, weak to moderate Bif-1 expression was observed in 53.8% (14/26) of cases and it was absent in 46.1% (12/26) of them. The BPH mean score was 1.6 (1.9 s.d.). Normal prostate tissues expressed low to moderate levels of Bif-1 in 89.5% of cases. Only 2 NR were Bif-1 negative. The NR mean score was 1.9 (1.4 s.d.). Strong Bif-1 expression was not noted in NR and BPH cases.

When comparing the differences in the staining scores between the TMA CA and TMA BPH, an adjusted p-value of 0.0060 was calculated. The difference in IHC score between TMA PIN and TMA BPH (p=<0.0001), TMA NR and TMA PIN (p=<0.0001), TMA PIN and TMA CA (p=0.003), TMA NR and TMA CA (p=0.049) were all statistically significant.

These results demonstrate a statistically significant difference in staining between prostatic hyperplasia, high grade PIN, and prostatic adenocarcinoma.

Antibody specificity: The specificity of the anti-Bif-1 monoclonal antibody was confirmed by immunoblot analysis of Bif-1-positive and –negative cells. As shown in FIG. 1, an approximately 41-kDa band corresponding to Bif-1 was detected in wild type cells. In contrast, this monoclonal antibody failed to react with any of the proteins in cell lysate prepared from Bif-1 knockout cells. The specificity of the anti-Bif-1 antibody was further confirmed by its reactivity with a single 41-kDa protein in Bif-1 knockout cells transfected with Bif-1 expression plasmid.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall there between. Now that the invention has been described, What is claimed is:

1. A method for detecting the presence of colorectal cancer, or prostate cancer within a sample, comprising:
    measuring a level of Bif-1 in a test sample of colon tissue, rectal tissue, or prostate tissue, wherein the test sample is suspected of being colorectal or prostate cancer;
    comparing the level of Bif-1 in the test sample to a reference level of Bif-1 from a reference sample; and
    establishing a ratio of Bif-1 levels in the sample based on the compared levels of Bif-1 in the test sample to the reference level of Bif-1;
        wherein a lower ratio of Bif-1 levels in the test sample relative to the reference level correlates with the presence of the neoplastic condition.

2. The method of claim 1, wherein the test sample is colon tumor tissue.

3. The method of claim 1, wherein the reference sample is normal tissue.

4. The method of claim 1, wherein the reference sample is taken from the same source as the test sample.

5. The method of claim 1, wherein the level of Bif-1 in a sample is selected from the group consisting of the level of a Bif-1 polypeptide in a sample and the level of Bif-1 gene expression in the sample.

6. The method of claim 1, wherein the level of Bif-1 in a sample is measured by an assay selected from the group consisting of detecting the expression of Bif-1 using a nucleic acid that specifically hybridizes to Bif-1 mRNA, detecting the expression of Bif-1 mRNA using primers that result in the amplification thereof and detecting the expression of Bif-1 protein using a monoclonal antibody or polyclonal antibody that specifically binds to Bif-1 polypeptide in the sample.

7. A method for detecting the presence of prostatic intraepithelial neoplasia within a sample, comprising:
    measuring a level of Bif-1 in a test sample of prostate tissue, wherein the test sample is suspected of being prostate cancer; and
    comparing the level of Bif-1 in the test sample to a reference level of Bif-1 from a reference sample;
        wherein a higher level of Bif-1 in the test sample relative to the reference level correlates with the presence of prostatic intraepithelial neoplasia.

8. The method of claim 7, wherein the reference sample is normal tissue.

9. The method of claim 7, wherein the reference sample is taken from the same source as the test sample.

10. The method of claim 7, wherein the level of Bif-1 in a sample is selected from the group consisting of the level of a Bif-1 polypeptide in a sample and the level of Bif-1 gene expression in the sample.

11. The method of claim 7, wherein the level of Bif-1 in a sample is measured by an assay selected from the group consisting of detecting the expression of Bif-1 using a nucleic acid that specifically hybridizes to Bif-1, detecting the expression of Bif-1 using primers that result in the amplification thereof and detecting the quantity of a monoclonal antibody or fragment that specifically binds to Bif-1 in the sample.

12. A method for detecting a precancerous prostatic neoplasia within a sample, comprising:
    measuring a level of Bif-1 in a test sample of prostate tissue, wherein the test sample is suspected of being prostate cancer;
    comparing the level of Bif-1 in the test sample to a reference level of Bif-1 from a reference sample; and
    establishing a ratio of Bif-1 levels in the sample based on the compared levels of Bif-1 in the test sample to the reference level of Bif-1;
        wherein a higher ratio of Bif-1 levels in the test sample relative to the reference level correlates with the presence of prostatic intraepithelial neoplasia.

13. The method of claim 7, wherein the reference sample is normal tissue.

14. The method of claim 7, wherein the reference sample is taken from the same source as the test sample.

15. The method of claim 7, wherein the level of Bif-1 in a sample is selected from the group consisting of the level of a Bif-1 polypeptide in a sample and the level of Bif-1 gene expression in the sample.

16. The method of claim 1, wherein the level of Bif-1 in a test sample is measured using semi-quantitative immunohistochemistry or microarray analysis.

17. The method of claim 1, wherein the reference level of Bif-1 in a reference sample is measured using semi-quantitative immunohistochemistry or microarray analysis.

18. The method of claim 1, wherein the reference sample is age-matched, sex-matched, matched to the patient's own tissue, or a combination thereof.

19. The method of claim 7, wherein the level of Bif-1 in a test sample is measured using semi-quantitative immunohistochemistry or microarray analysis.

20. The method of claim 7, wherein the reference level of Bif-1 in a reference sample is measured using semi-quantitative immunohistochemistry or microarray analysis.

21. The method of claim 12, wherein the level of Bif-1 in a test sample is measured using semi-quantitative immunohistochemistry or microarray analysis.

22. The method of claim 12, wherein the reference level of Bif-1 in a reference sample is measured using semi-quantitative immunohistochemistry or microarray analysis.

23. The method of claim 12, wherein the reference sample is age-matched, sex-matched, matched to the patient's own tissue, or a combination thereof.

\* \* \* \* \*